(12) United States Patent
Sarver et al.

(10) Patent No.: US 6,607,273 B2
(45) Date of Patent: Aug. 19, 2003

(54) STEREO VIEW REFLECTION CORNEAL TOPOGRAPHY

(75) Inventors: Ed Sarver, Merritt Island, FL (US); David Liu, Winter Springs, FL (US)

(73) Assignee: Lasersight Technologies, Inc., Winter Park, FL (US)

( * ) Notice: Subject to any disclaimer, the term of this patent is extended or adjusted under 35 U.S.C. 154(b) by 92 days.

(21) Appl. No.: 09/978,657

(22) Filed: Oct. 18, 2001

(65) Prior Publication Data

US 2002/0044258 A1 Apr. 18, 2002

Related U.S. Application Data

(60) Provisional application No. 60/283,627, filed on Apr. 16, 2001, provisional application No. 60/283,625, filed on Apr. 16, 2001, and provisional application No. 60/240,983, filed on Oct. 18, 2000.

(51) Int. Cl.[7] ................................. A61B 3/10
(52) U.S. Cl. ..................................................... 351/212
(58) Field of Search ................................. 351/205, 206, 351/211, 212, 240, 246, 221; 356/124, 125; 359/835, 376; 606/4, 5

(56) References Cited

U.S. PATENT DOCUMENTS 5,535,060 A * 7/1996 Grinblat ..................... 359/835

\* cited by examiner

*Primary Examiner*—George Manuel

(57) ABSTRACT

A stereo target corneal topography apparatus and method that uses two differently angled views of a target pattern reflected from a cornea to measure the shape of a cornea using a stereo reconstruction module to reconstruct the shape of a surface of a cornea. The surface elevation, surface slope and/or surface power may be determined without the need to make an initial assumption about the shape of the cornea.

40 Claims, 11 Drawing Sheets

STEREO VIEW REFLECTION CORNEAL TOPOGRAPHY

This application claims priority from U.S. Provisional Appl. No. 60/240,983, entitled "Stereo View Reflection Corneal Topography," filed Oct. 18, 2000, U.S. Provisional Appl. No. 60/283,625, entitled "Stereoscopic Measurement of Corneal Thickness, Anterior Chamber Depth, Thickness Of The Intra-Ocular Lens And/Or The Curvature Of The Lens And The Opacity of the Lens," filed Apr. 16, 2001, and U.S. Provisional Appl. No. 60/283,627, entitled "Illumination Pattern for the Cornea, Anterior Chamber and Intra-Ocular Lens Measurement Using Stereo Imaging of One of a Few Rapid Acquisitions," filed on Apr. 16, 2001, as well as from U.S. appl. Ser. No. 09/860,558, entitled "Combination Advanced Topography/Wave Front Aberration Measurement," filed May 21, 2001, which claims priority from U.S. Pat. No. 6,234,631, entitled "Combination Advanced Corneal Topography/Wave Front Aberration Measurement" to Sarver et al., filed Mar. 9, 2000, the entirety of all of which are expressly incorporated herein by reference.

BACKGROUND OF THE INVENTION

1. Field of the Invention

This invention relates generally to non-destructive surface measurement. More particularly, it relates to the measurement of surface elevation, surface slope, and/or optical power of the human cornea.

2. Background

The cornea, the front surface of the eye, provides about two-thirds of the eye's refractive power and therefore is important to quality of vision. Accurate measurement of the shape of the human cornea is of great concern in the field of ophthalmology and optometry. The accuracy of these measurements directly affects the ability to detect early cornea disease, accurately fit hard contact lenses, and compute the correct power for a phakic or aphakic intraocular lens. Most importantly, accurate measurement of a cornea, including minor surface imperfections, is critical to perform successful custom corneal refractive laser surgery to correct myopia or hyperopia.

One method of measuring the shape of the anterior cornea, which is widely used today, is a reflected target corneal topography system, e.g., as shown in FIG. 10. Using this reflected target system, corneal topography is typically measured using a series of concentric lighted rings, known as a keratoscope pattern.

FIGS. 10 and 10A show a conventional monocular corneal topography system.

In particular, as shown in FIG. 10, an illumination source (not shown) projects infrared rays through a keratoscope target 1010, which comprises, e.g., illuminated concentric rings, as shown in FIG. 10A. The rays are projected onto the cornea 1012 of a patient's eye 1014. The cornea in part reflects the rays. A front view camera with lens 1006 captures the rays and focuses them onto a CCD 1004. The rays are in the form of a keratoscope pattern 1008, e.g., a reflected image of rings. A computer 1002 processes the image to detect the rings, to apply a reconstruction algorithm to extract elevation and slope or curvature data, and to generate and display a color-coded contour map for interpretation by a health care professional.

Typical methods used by these instruments make some assumptions about the shape of the cornea to reconstruct and extract the desired data. Assumptions are required due to the non-unique nature of the acquired image.

For example, FIG. 11 depicts an exemplary problem of computing surface points using a conventional monocular reflective corneal topography technique and apparatus.

In particular, as shown in FIG. 11, a given target point T1 is reflected off the cornea 1012 and captured by a lens L1. In the digital reconstruction of the image, there are, e.g., three possible "surface" points, S1, S2 and S3, with different elevations and surface normals, that could have reflected target point T1. In this example, only surface point S2 is correct because it is the only point actually located on the surface of the cornea. Therefore, a method is required to select a "best" surface point.

A conventional assumption is that the curvature between data points is constant. This was the assumption made by several researchers and manufacturers including Wang (Wang 1998), Klein (1992), Campbell (1997), van Saarloos (1991), Mattioli (1997), and Brenner (1997).

However, the assumption of constant curvature is not entirely satisfactory because it can lead to errors that accumulate, as pointed out by the same researchers. Some attempts to overcome these limitations have had some success (e.g., Halstead et al., (1995) and Klein (1992)), but have not been shown to be clinically viable.

One approach by Sarver and Broadus (U.S. Pat. No. 6,079,831) combines both scanning slit and reflection target techniques. This approach represents an improvement on the accuracy of previous corneal topography instruments, but the resulting instrument is complex and expensive to produce.

There is a need for an improved reflective target corneal topography technique and apparatus that is simple to produce and that provides superior measurement results.

SUMMARY OF THE INVENTION

An improved reflective target corneal topography system includes a stereo image reconstructor that generates surface elevation data, surface normal data, and surface power data without the traditional need for assumptions about the shape of the surface being tested. The reflective target corneal topography system further includes stereo optics, with image detection devices in each optical device, to preferably allow substantially simultaneous stereo image acquisitions.

BRIEF DESCRIPTION OF THE DRAWINGS

Features and advantages of the present invention will become apparent to those skilled in the art from the following description with reference to the drawings, in which.

DETAILED DESCRIPTION OF ILLUSTRATIVE EMBODIMENTS

Figure 1:
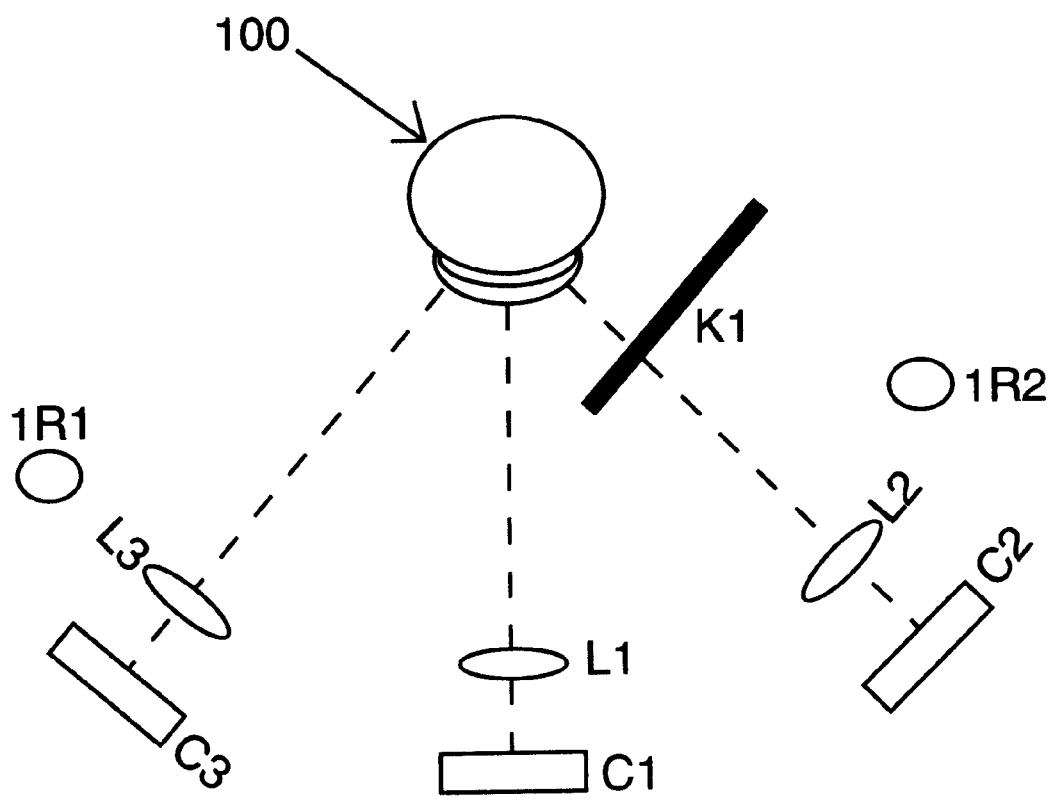
FIG. 1 shows an exemplary block diagram of a stereo corneal topography system, in accordance with the principles of the present invention.

FIG. 1 shows an exemplary block diagram of a stereo corneal topography system, in accordance with the principles of the present invention.

As shown in FIG. 1, the system comprises a keratometric target source K1 with an illumination source (not shown). There are two infrared illumination sources IR1 and IR2, three cameras C1, C2 and C3 with respective camera lenses L1, L2 and L3, and a computer (not shown) with video digitizer card(s). In this exemplary embodiment, camera C1 is oriented along an optical axis of the eye 100 and cameras C2 and C3 are oriented at skew angles with respect to the eye 100. Three cameras are shown because this increases the coverage area of the cornea, although the use of only one camera obtaining data at different views or of only two cameras is within the scope of the present invention.

In accordance with the principles of the present invention, the keratometric target source K1 is reflected off a cornea and imaged by at least two of the cameras. These digitized images are processed as explained below.

Basic Geometry

Figure 2:
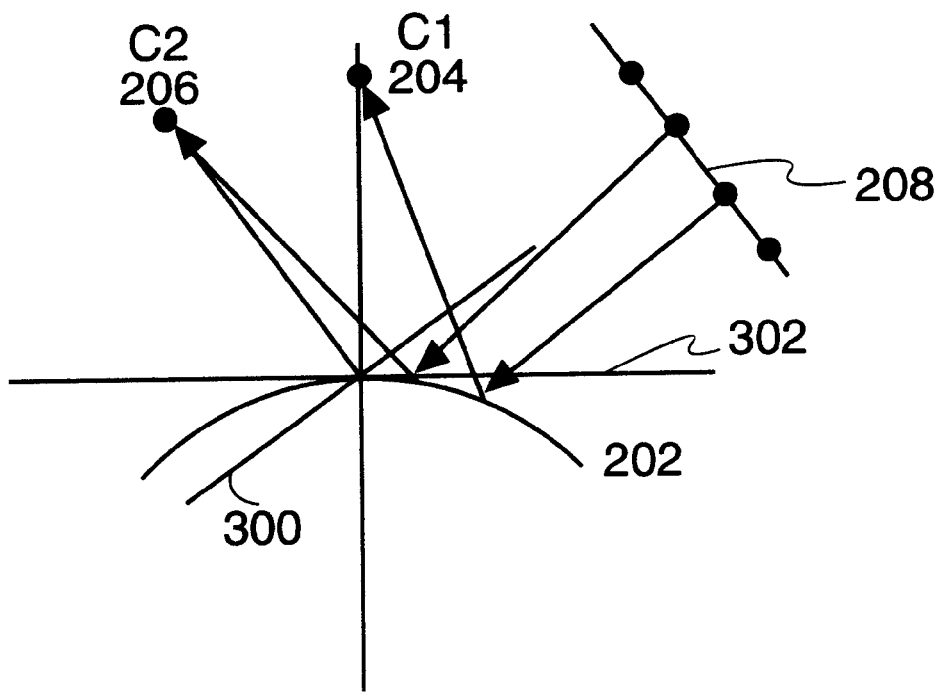
FIG. 2 shows basic geometry for an exemplary stereo corneal topography system, in accordance with the principles of the present invention.

FIG. 2 shows basic geometry for an exemplary stereo corneal topography system, such as that shown in FIG. 1, in accordance with the principles of the present invention.

In particular, as shown in FIG. 2, a target 208 includes target features such as concentric rings, checkered placido, etc. An exemplary checkered placido method and apparatus is shown and described in U.S. Pat. No. 6,213,605, the entirety of which is expressly incorporated herein by reference. Camera 1 C1 is located at point 204 and camera 2 C2 is located at point 206. A surface 202 is under test.

While camera 1 C1 and camera 2 C2 are shown in FIG. 2, the principles of the present invention relate equally to the use of more than two cameras to obtain additional coverage of the surface under test 202 and to obtain additional data.

The surface under test 202 is measured by reflecting a target pattern 208 off the reflective surface under test 202, detecting the reflected pattern with at least two cameras C1 and C2, and analyzing the ray correspondence between the captured reflected images and known target point locations.

Figure 3:
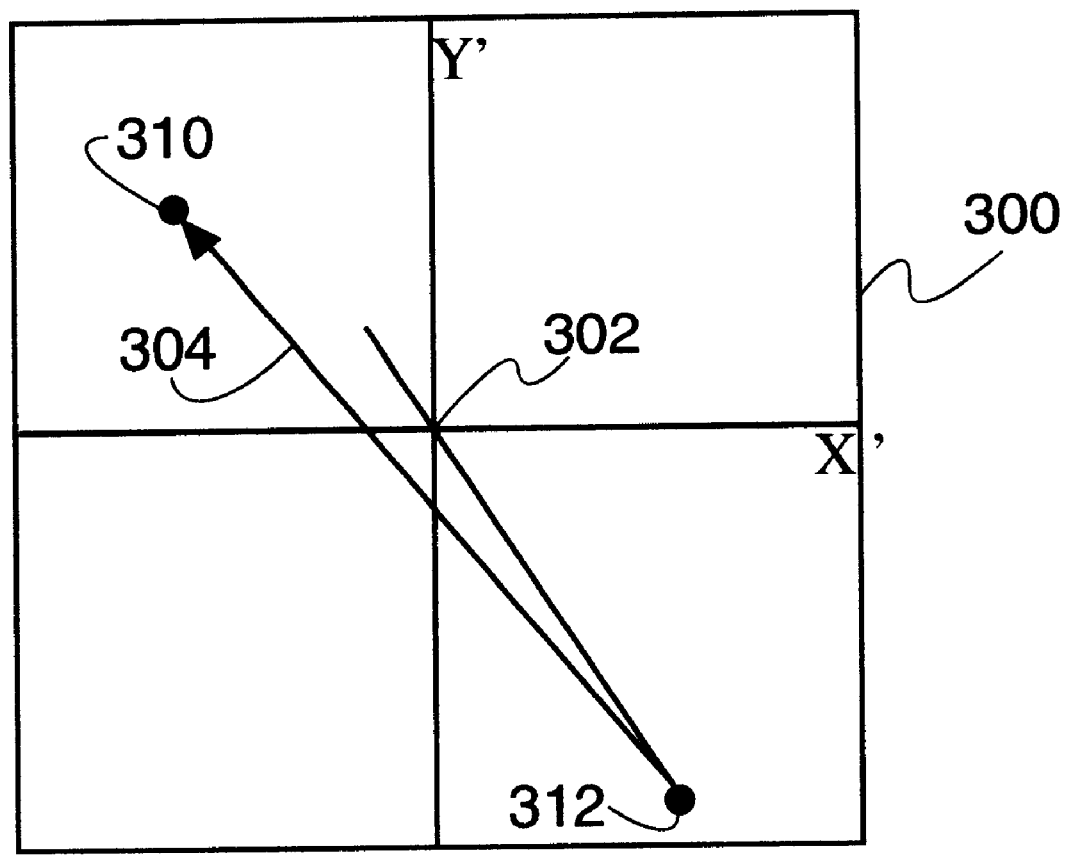
FIG. 3 shows an exemplary focal plane of camera 2 shown in FIG. 2.

FIG. 3 shows an exemplary focal plane 300 of camera 2 206 shown in FIG. 3. If more than two cameras are present in the system, each of the additional cameras may have a focal plane such as that shown in FIG. 3.

In FIG. 3, the coordinates of the focal plane 300 are referred to as X' and Y', and have the optical axis of the camera C2 as the origin 302. Ray 304 pointed in the upper left quadrant of the focal plane 300 indicates that a target point 310 reflected from surface point 312 has been identified via image processing. All target points may be detected using standard image processing techniques.

From system design and calibration procedures, the location of each detected target point 310 is preferably known. Using these known target points, remaining target points may be interpolated as to their location in the skew camera focal plane image 300. This information is used in a reconstructor module as explained below.

Basic Image Processing

Basic image processing performed in an image stereo image reconstructor in accordance with the disclosed embodiments may be the same as that performed by otherwise conventional reflective target corneal topography systems. For instance, such image processing may typically use edge or peak detection, center finding, and sub-pixel feature location techniques as detailed in any current text on image processing. The stereo images captured are reconstructed as discussed below.

Stereo Axial Arc Step Reconstruction

Figure 4:
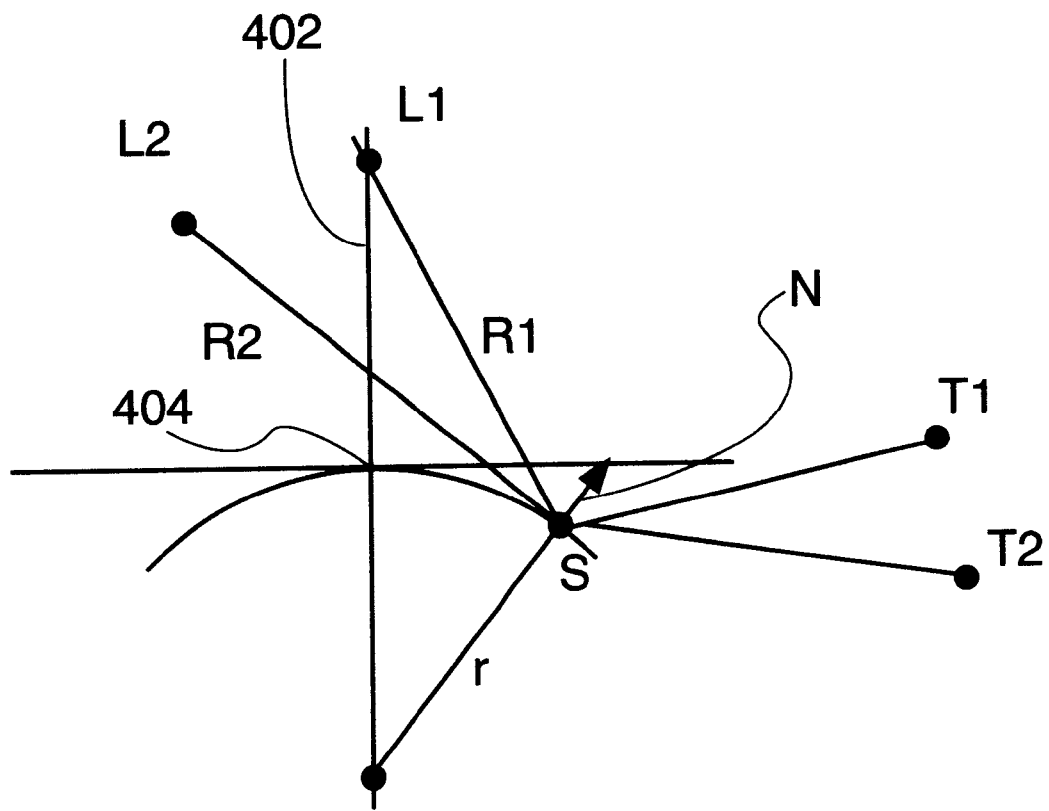
FIG. 4 shows exemplary geometry for a stereo axial arc step reconstructor, in accordance with the principles of the present invention.

FIG. 4 shows exemplary geometry for a stereo axial arc step reconstructor, in accordance with the principles of the present invention. The reconstructor includes a stereo image reconstructor that may be any suitable stereo image reconstructor, e.g., a microcontroller, a microstereo image reconstructor, or a digital signal stereo image reconstructor.

In particular, FIG. 4 shows lenses L1 and L2. In accordance with the principles of the present invention, the stereo axial arc reconstructor uses a reconstructions algorithm to compute a point S on the surface of a cornea, a surface normal N for point S, and axial radius r (which is the extension of the surface normal for point S to the intersection of the vertical axis 402) by finding points T1 and T2 on the keratoscope target and calculating rays R1 and R2 (which are the rays from surface point S to Lenses L1 and L2).

The reconstruction algorithm is initialized by placing a surface point of the apex 404 of the cornea at the origin of the coordinate system, and making the assumption that the surface normal 402 at the apex is parallel with the optical axis of Lens L1.

Figure 5:
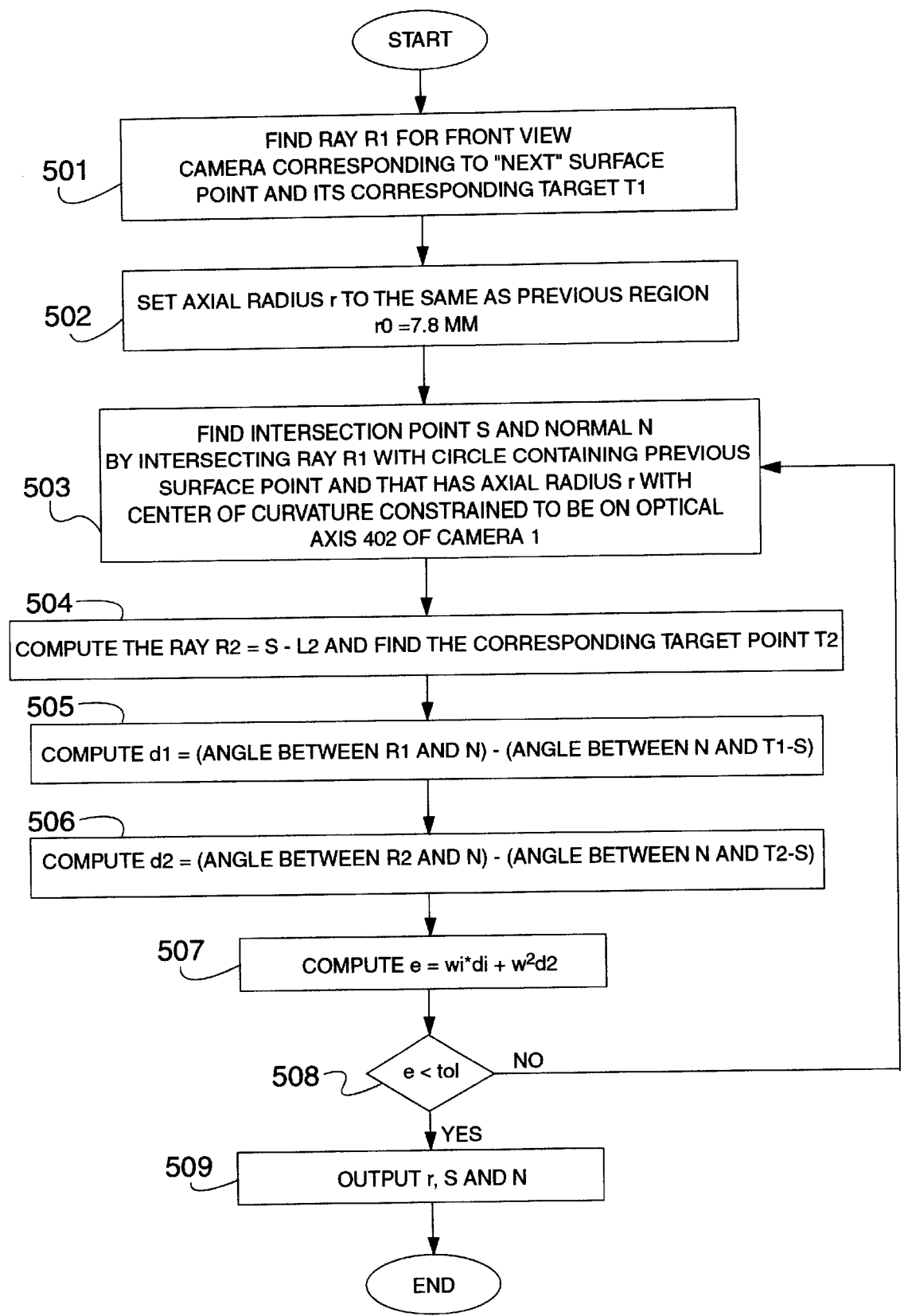
FIG. 5 shows steps in an exemplary process of computing the surface point, surface normal, and axial radius associated with subsequent points.

FIG. 5 shows steps in an exemplary process of computing the surface point S, surface normal N, and axial radius r associated with subsequent points.

In particular, as shown in FIG. 5, in Step 501, it is necessary to find the ray R1 for the front view camera that corresponds to the "next" surface point and also to find its corresponding target point T1.

In Step 502, the reconstructor sets axial radius r to be the same as the axial radius for the previous point. The first point is set at r=7.8 mm, the average axial radius.

In Step 503, ray R1 is intersected with a circle that contains the previous surface point and has the axial radius r. The center of curvature is constrained to be on the optical axis 402 of camera C1. This intersection point is S. The normal at this point is N.

In Step 504, the reconstructor computes the ray R2=S−L2, and then finds the corresponding target point T2.

In Step 505, the reconstructor computes d1, which equals the angle between R1 and N less the angle between N and T1-S.

In Step 506, the reconstructor computes d2, which equals the angle between R2 and N less the angle between N and T2-S.

In Step 507, the reconstructor computes the amount of error e by multiplying a weighting factor w1 times d1, multiplying a weighting factor w2 times d2 and then combining the product of the two. The weighting factors are set in advance in accordance with the precision required of the system for the particular measurements.

In Step 508, the reconstructor compares the error e with the allowed tolerance tol, which is determined from calibration of the system. If the error e is less than or equal to the tolerance tol, then the reconstructor outputs r, S, and N. If the error e is not within the tolerance, then in step 509, the reconstructor adjusts radius r using Newton iteration and repeats the algorithm beginning at step 503.

Stereo Instantaneous Arc Step Reconstruction

Figure 6:
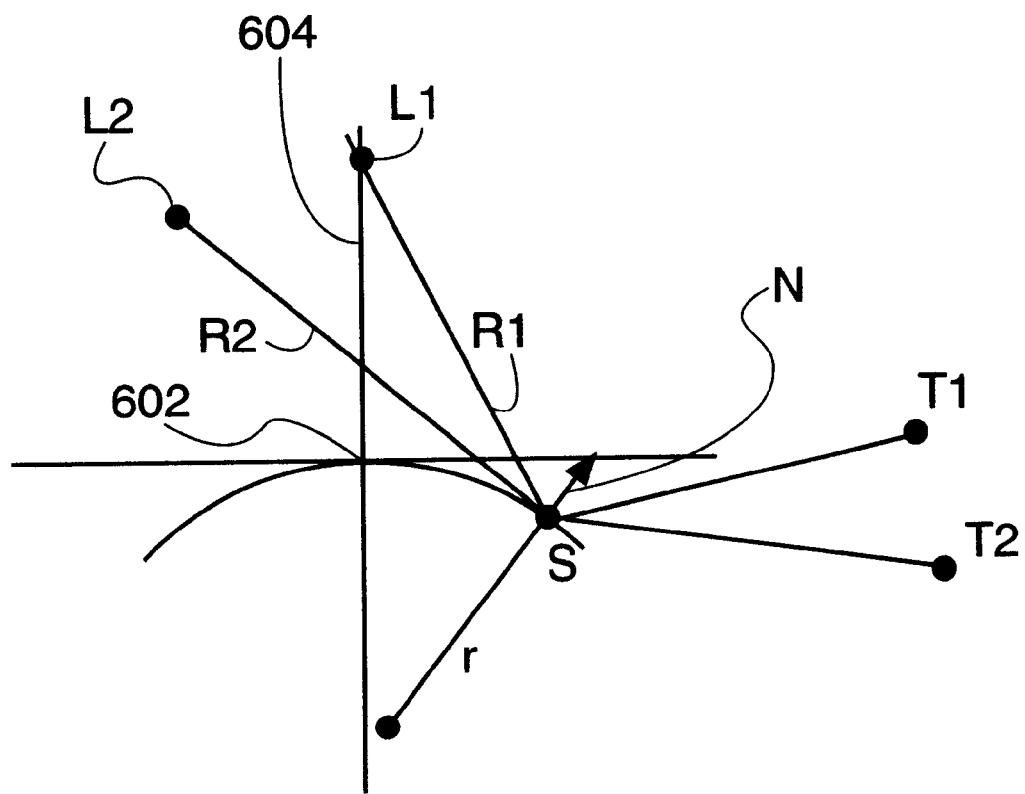
FIG. 6 shows an exemplary geometry for a stereo instantaneous arc step reconstructor, in accordance with the principles of the present invention.

FIG. 6 shows exemplary geometry for a stereo instantaneous arc step reconstructor, in accordance with the principles of the present invention. The reconstructor comprises a stereo image reconstructor, which may be any suitable stereo image reconstructor, e.g., a microcontroller, a microstereo image reconstructor, or a digital signal stereo image reconstructor.

In particular, FIG. 6 shows Lenses L1 and L2. In accordance with the principles of the present invention, the stereo instantaneous arc step reconstructor uses a reconstruction algorithm that will compute point S on the surface of a cornea, surface normal N for point S, instantaneous radius of curvature r (which is the extension of the surface normal N for point S and an end point calculated by the reconstructor for the instantaneous arc or slope at point S, which as shown in FIG. 6 is not necessarily on vertical axis 604) by finding points T1 and T2 on the keratoscope target and calculating rays R1 and R2 (which are the rays from surface point S to Lenses L1 and L2). Instantaneous arc step reconstruction refers to determining the instantaneous arc or slope at a particular point (as opposed to axial arc step reconstruction, which as explained above finds the arc between two closely spaced points).

The stereo instantaneous arc step reconstructor is initialized by placing the surface point of the apex 602 of the cornea at the origin of the coordinate system and making the assumption that the surface normal 604 at the apex is parallel with the optical axis of Lens L1.

Figure 7:
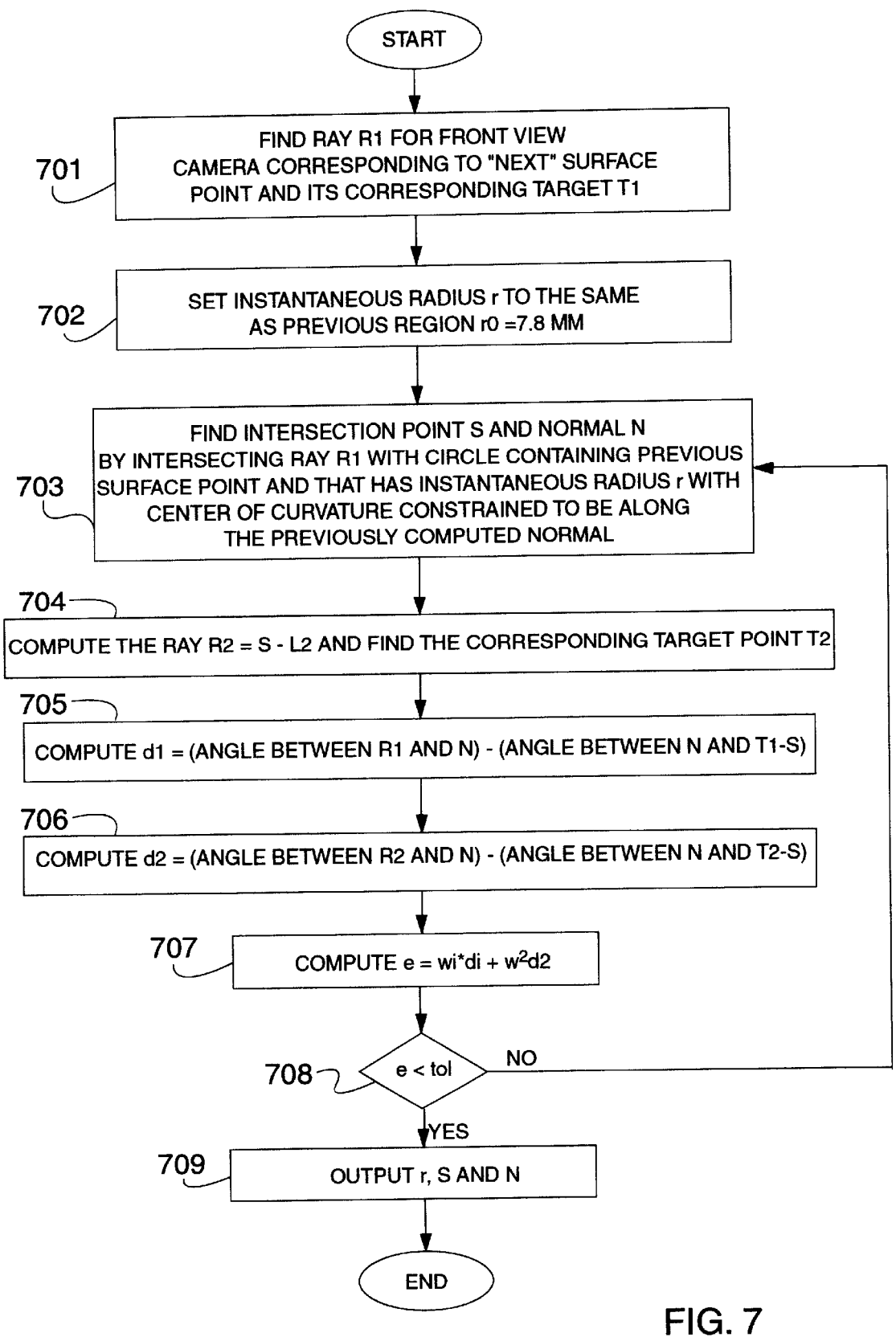
FIG. 7 shows steps in an exemplary process of computing the surface point, surface normal, and instantaneous radius of curvature associated with subsequent points.

FIG. 7 shows steps in an exemplary process of computing the surface point S, surface normal N, and instantaneous radius of curvature r associated with subsequent points.

In particular, as shown in FIG. 7, in step 701, it is necessary to find the ray R1 for the front view camera that corresponds to the "next" surface point and also to find its corresponding target point T1.

In Step 702, the instantaneous radius r is set to be the same as the instantaneous radius for the previous point. The first point is set at r=7.8 mm, the average radius.

In Step 703, ray R1 is intersected with the circle that contains the previous surface point and that has the instantaneous radius r. The center of curvature is constrained to be along the previously computed normal. This intersection point is S. The normal at this point is N.

In Step 704, the reconstructor computes the ray R2=S−L2, and find the corresponding target point T2.

In Step 705, the reconstructor computes d1, which is the angle between R1 and N less the angle between N and T1-S.

In Step 706, the reconstructor computes d2, which is the angle between R2 and N less the angle between N and T2-S.

In Step 707, an error e is computed by multiplying the weighting factor w1 times d1, multiplying the weighting factor w2 times d2, and adding the two products. As noted, the weighting factors are set in advance depending on the precision required of the system.

In Step 708, the reconstructor compares error e to the allowed tolerance tol, which is determined in advance from system calibration. If error e is less than or equal to the allowed tolerance tol, then the reconstructor outputs r, S and N. If the error is greater than the allowed tolerance, then in Step 709, r is adjusted (e.g., using Newton iteration) and the algorithm is repeated beginning at Step 703.

Stereo Constraint-free Reconstruction

Figure 8:
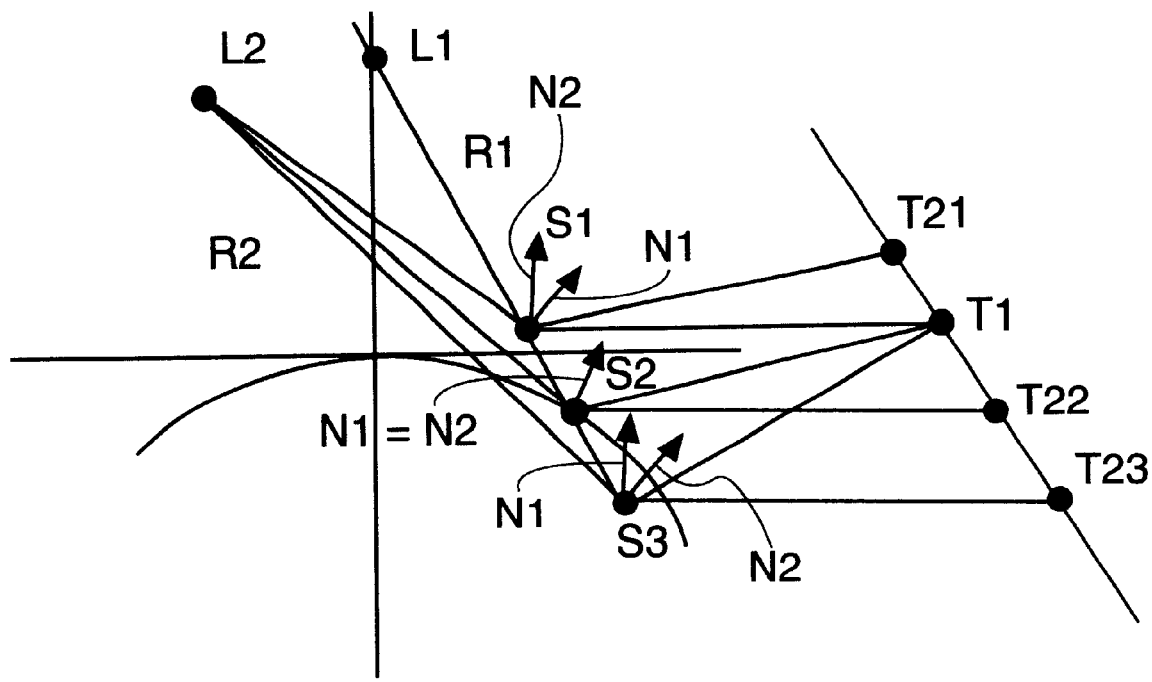
FIG. 8 shows an exemplary geometry for a constraint-free reconstructor, in accordance with the principles of the present invention.

FIG. 8 shows an exemplary geometry for a constraint-free reconstructor, in accordance with the principles of the present invention.

In particular, FIG. 8 shows lenses L1 and L2. Point T1 is a target point on the keratoscope target. Points T21, T22 and T23 are target points on the keratoscope target that correspond to possible surface points S1, S2 and S3. The arrows pointing out from S1, S2 and S3 are normals for the reflected target points. Normals N1 are the normals for the angles defined as L1 to possible surface points S1, S2 and S3 to targets point T1. Normals N2 are the normals for the angles defined as L2 to possible surface points S1, S2 and S3 to possible targets points T21, T22 and T23. When surface point S2 is calculated, normal N1 will substantially equal N2, as shown in FIG. 8. Ray R1 is the ray of point T1 reflected from the cornea to lens L1. Ray R2 is the ray of possible target points T21, T22 and T23 reflected off possible surface points S1, S2 and S3 to lens L2.

The determination of which surface point is on the cornea is accomplished by determining, in accordance with the principles of the present invention, which surface point has only one normal for target points T1 and T2. In this exemplary geometry, surface point S2 is the true surface point because it has only one normal.

In accordance with the principles of the present invention, the stereo constraint-free reconstructor uses a reconstruction algorithm that, unlike previous reconstruction techniques, does not make any assumptions regarding the shape of the surface between detected target points for lens L1. For instance, the data may be computed in any order. The data computed directly from this method are surface location and slope (or instantaneous arc). This data may be directly used as constraints in a surface fitting strategy using, for example, 2D Taylor polynomials, 2D B-Splines, or Zernike Polynomials. Additionally, the axial or instantaneous radius values can be computed from either the raw data, interpolated data, or from the fitted surface.

Figure 9:
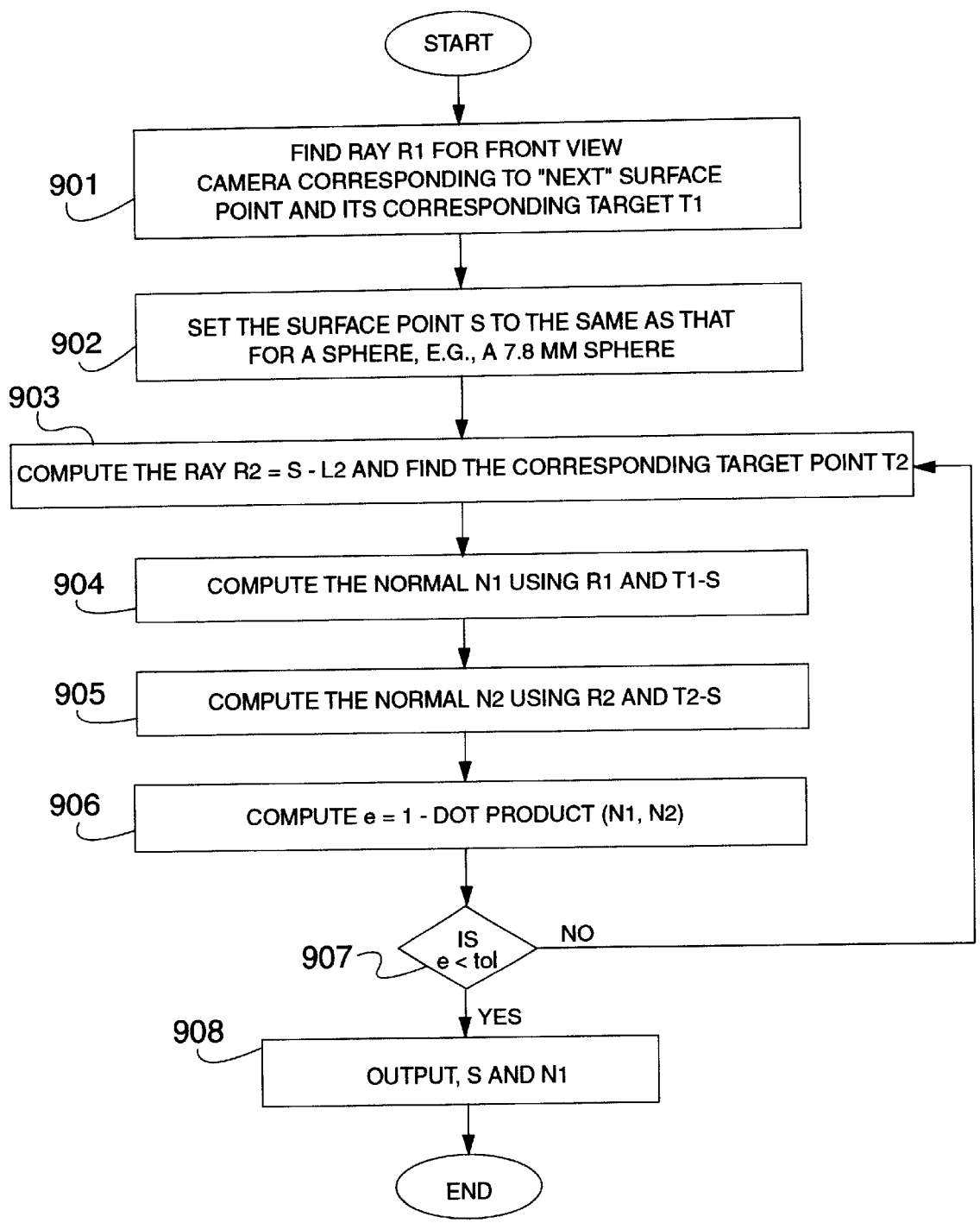
FIG. 9 shows a reconstruction technique for a given point for the system shown in FIG. 8.
Figure 10:
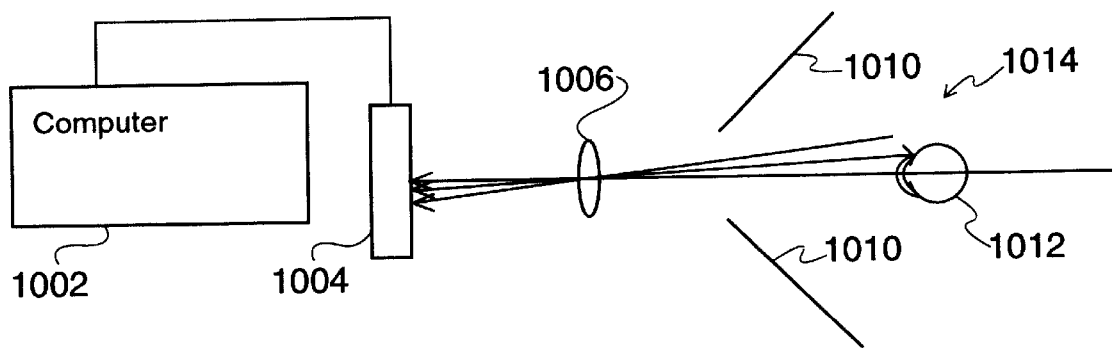
FIGS. 10 and 10A are a representation of a conventional monocular corneal topography system.
Figure 10A:
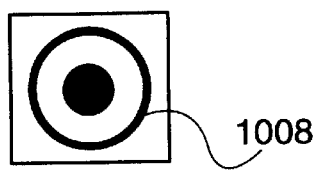
Figure 11:
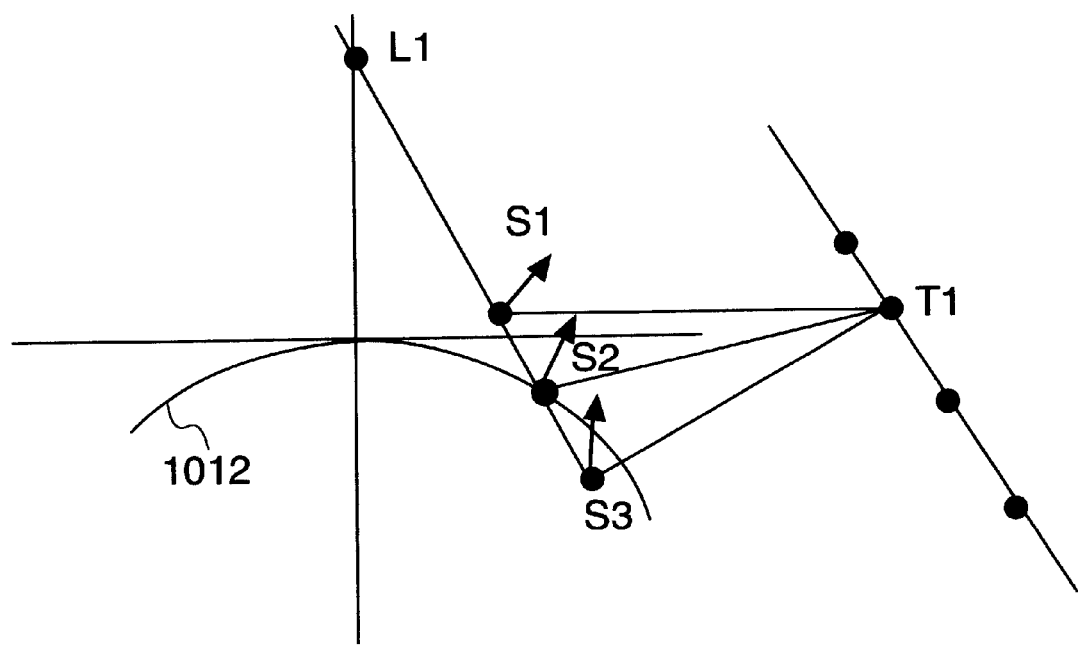
FIG. 11 shows an exemplary problem of computing the surface point using a conventional monocular reflective corneal topography technique.

FIG. 9 shows exemplary steps in an exemplary process of constraint-free reconstruction for a given point for the system shown in FIG. 8.

In Step 901, it is necessary to find the ray R1 for the front view camera that corresponds to the "next" surface point and then find its corresponding target point T1.

In Step 902, the surface point S is set to be the same as that for a sphere, e.g., a 7.8 mm sphere.

In Step 903, the reconstructor computes the ray R2=S−L2, and finds the corresponding target point T2.

In Step 904, the reconstructor computes the normal N1 using R1 and T1−S and in Step 905, it computes the normal N2 using R2 and T2−S.

In Step 906, the reconstructor computes error e=1−dot product (N1, N2). This will give a signed error.

In Step 907, if error e is less than the predetermined tolerance tol, then the reconstructor outputs S and N1. If error e is greater than the predetermined tolerance tol, then the reconstructor adjusts the surface S along R1 and goes back to step 903.

The image processing of the digitized target reflection image preferably allows for the unique correspondence of points in the image to points on the target source. For patterns that provide for this unique correspondence, no special processing is required beyond the image process detection phase.

For traditional concentric ring target patterns, an approximation to the surface under test can be obtained from processing the front image alone, and can be used to estimate the location of the meridians in the target pattern that are digitized by the skew view camera(s). This additional step is required only to permit the use of the traditional concentric ring patterns.

For regular, smooth and monotonic surfaces, mono-view reconstruction is usually adequate. For irregular surfaces, stereo view reconstruction is preferred for accurate measurement. Thus, an exemplary fast processing strategy is as follows:

1) Reconstruct the surface using mono-view;
2) Check subset of reconstructed points using stereo information; and
3) If the difference is greater than certain predefined threshold, then use stereo reconstruction to correct the mono-view reconstruction error.

While the invention has been described with reference to the exemplary embodiments thereof, those skilled in the art will be able to make various modifications to the described embodiments of the invention without departing from the true spirit and scope of the invention.

What is claimed is:

1. A stereo target corneal topography system comprising:
    a target source illuminated by at least one illumination source to generate a target pattern;
    at least two camera views oriented at different angles with respect to a cornea to be measured; and
    a stereo image reconstructor to reconstruct a shape of said cornea from at least two differently angled views of said target pattern reflected from said cornea.

2. The stereo target corneal topography system according to claim 1, wherein:
    said target source is a keratometric target source.

3. The stereo target corneal topography system according to claim 1, wherein said stereo image reconstructor comprises:
    a stereo axial arc-step module to reconstruct at least one of a surface elevation, a surface slope, and a surface power at a point on said cornea.

4. The stereo target corneal topography system according to claim 1, wherein said stereo image reconstructor comprises:
    a stereo instantaneous arc-step module to reconstruct at least one of a surface elevation, a surface slope, and a surface power at a point on said cornea.

5. The stereo target corneal topography system according to claim 1, wherein said stereo image reconstructor comprises:
    a stereo constraint-free module to reconstruct at least one of a surface elevation, a surface slope, and a surface power at a point on said cornea.

6. The stereo target corneal topography system according to claim 1, wherein:
    said stereo image reconstructor includes a module to compute a point correspondence between a given ray and a target point by interpolating from a surface.

7. The stereo target corneal topography system according to claim 1, wherein:
    said stereo image reconstructor includes a module to compute a point correspondence between a given ray and a target point by directly interpolating data.

8. The stereo target corneal topography system according to claim 1, wherein:
    said stereo image reconstructor includes an iterative processor to improve calculation accuracy.

9. The stereo target corneal topography system according to claim 1, wherein said at least two camera views comprise:
    a single camera repositioned between at least two differently angled views.

10. The stereo target corneal topography system according to claim 1, wherein said at least two camera views comprise:
    a first camera oriented at a first angle with respect to an optical axis of said cornea; and
    a second camera oriented at a second angle different from said first angle with respect to said optical axis of said cornea.

11. The stereo target corneal topography system according to claim 10, wherein:
    said first camera is oriented along said optical axis of said cornea.

12. The stereo target corneal topography system according to claim 11, wherein:
    said stereo image reconstructor calculates a prediction of meridians on said target pattern from a surface approximation obtained from only said first camera.

13. A stereo reconstructor used to measure a shape of a cornea, comprising:
    a processor arranged and adapted to reconstruct said shape of a surface of said cornea using data obtained from at least two differently angled views of a target pattern reflected from said cornea.

14. The stereo reconstructor according to claim 13, wherein said processor includes:
    a stereo axial arc-step module to reconstruct at least one of a surface elevation, a surface slope and a surface power at a point on said cornea.

15. The stereo reconstructor according to claim 13, wherein said processor includes:
    a stereo instantaneous arc-step module to reconstruct at least one of a surface elevation, a surface slope and a surface power at a point on said cornea.

16. The stereo reconstructor according to claim 13, wherein said processor includes:
    a stereo constraint free module to reconstruct at least one of a surface elevation, a surface slope and a surface power at a point on said cornea.

17. The stereo reconstructor according to claim 13, wherein:
    said processor computes a point correspondence between a given ray and a target point by interpolating from a surface.

18. The stereo reconstructor according to claim 13, wherein:
    said processor computes a point correspondence between a given ray and a target point by directly interpolating data.

19. The stereo reconstructor according to claim 13, wherein:
    said processor uses iterative processing to improve calculation accuracy.

20. The stereo reconstructor according to claim 13, wherein:
    said processor calculates a prediction of meridians on said target pattern from a surface approximation obtained from only a view along an optical axis of said cornea.

21. A method of reconstructing a shape of a cornea, comprising:
    obtaining at least two differently angled views of a keratometric target pattern reflected from said cornea; and reconstructing said shape of said cornea using data obtained from said at least two differently angled views of said reflected target pattern.

22. The method of reconstructing a shape of a cornea according to claim 21, wherein:
said reconstructing uses a stereo axial arc-step technique to reconstruct at least one of a surface elevation, a surface slope and a surface power at a point on said cornea.

23. The method of reconstructing a shape of a cornea according to claim 21, wherein:
said reconstructing uses a stereo instantaneous arc-step technique to reconstruct at least one of a surface elevation, a surface slope and a surface power at a point on said cornea.

24. The method of reconstructing a shape of a cornea according to claim 21, wherein:
said reconstructing uses a stereo constraint free technique to reconstruct at least one of a surface elevation, a surface slope and a surface power at a point on said cornea.

25. The method of reconstructing a shape of a cornea according to claim 21, wherein:
said reconstructing computes a point correspondence between a given ray and a target point by interpolating from a surface.

26. The method of reconstructing a shape of a cornea according to claim 21, wherein:
said reconstructing computes a point correspondence between a given ray and a target point by directly interpolating data.

27. The method of reconstructing a shape of a cornea according to claim 21, wherein:
said reconstructing uses iterative processing to improve calculation accuracy.

28. The method of reconstructing a shape of a cornea according to claim 21, wherein:
said reconstructing uses traced optical rays from at least two differently angled cameras at a same time.

29. The method of reconstructing a shape of a cornea according to claim 21, wherein:
said reconstructing uses traced optical rays from at least two differently angled cameras by sequential processing.

30. The method of reconstructing a shape of a cornea according to claim 21, wherein:
said reconstructing calculates a prediction of meridians on the target from a surface approximation obtained from only a view along an optical axis of said cornea.

31. A stereo target corneal topography device, comprising:
means for obtaining at least two differently angled views of a target pattern reflected from said cornea; and
means for reconstructing a shape of said cornea using data obtained from said at least two differently angled views of said reflected target pattern.

32. The stereo target corneal topography device according to claim 31, wherein said means for reconstructing comprises:
a stereo axial arc-step module to reconstruct at least one of a surface elevation, a surface slope and a surface power at a point on said cornea.

33. The stereo target corneal topography device according to claim 31, wherein said means for reconstructing comprises:
a stereo instantaneous arc-step module to reconstruct at least one of a surface elevation, a surface slope and a surface power at a point on said cornea.

34. The stereo target corneal topography device according to claim 31, wherein said means for reconstructing comprises:
a stereo constraint free module to reconstruct at least one of a surface elevation, a surface slope and a surface power at a point on said cornea.

35. The stereo target corneal topography device according to claim 31, wherein:
said means for reconstructing computes a point correspondence between a given ray and a target point by interpolating from a surface.

36. The stereo target corneal topography device according to claim 31, wherein:
said means for reconstructing computes a point correspondence between a given ray and a target point by directly interpolating data.

37. The stereo target corneal topography device according to claim 31, wherein:
said means for reconstructing uses iterative processing to improve calculation accuracy.

38. The stereo target corneal topography device according to claim 31, wherein:
said means for reconstructing uses traced optical rays from at least two differently angled cameras at a same time.

39. The stereo target corneal topography device according to claim 31, wherein:
said means for reconstructing uses traced optical rays from at least two differently angled cameras by sequential processing.

40. The stereo target corneal topography device according to claim 31, wherein:
said means for reconstructing calculates a prediction of meridians on said target from a surface approximation obtained from only a view along an optical axis of said cornea.

* * * * *